United States Patent
Trapp et al.

(10) Patent No.: US 12,167,983 B2
(45) Date of Patent: Dec. 17, 2024

(54) SUPPORTING ARM SYSTEM FOR A MEDICAL DEVICE, METHOD FOR OPERATING A SUPPORT ARM SYSTEM FOR A MEDICAL DEVICE, METHOD FOR OPERATING A SUPPORT ARM SYSTEM, AND METHOD FOR DESIGNING A SUPPORT ARM SYSTEM

(71) Applicant: ONDAL MEDICAL SYSTEMS GMBH, Hünfeld (DE)

(72) Inventors: Markus Trapp, Hauneck Rotensee (DE); André Pforr, Hünfeld (DE)

(73) Assignee: ONDAL MEDICAL SYSTEMS GMBH, Hünfeld (DE)

( * ) Notice: Subject to any disclaimer, the term of this patent is extended or adjusted under 35 U.S.C. 154(b) by 862 days.

(21) Appl. No.: 17/289,798

(22) PCT Filed: Oct. 31, 2019

(86) PCT No.: PCT/EP2019/079935
§ 371 (c)(1),
(2) Date: Apr. 29, 2021

(87) PCT Pub. No.: WO2020/094518
PCT Pub. Date: May 14, 2020

(65) Prior Publication Data
US 2021/0393465 A1  Dec. 23, 2021

(30) Foreign Application Priority Data
Nov. 5, 2018  (EP) ..................... 18204371

(51) Int. Cl.
*A61G 13/10* (2006.01)
*A61B 34/30* (2016.01)
(Continued)

(52) U.S. Cl.
CPC .............. *A61G 13/10* (2013.01); *A61B 34/30* (2016.02); *A61B 90/35* (2016.02); *A61B 90/50* (2016.02);
(Continued)

(58) Field of Classification Search
CPC ................ A61G 13/10; A61G 2203/32; A61G 2203/36; A61G 2203/726; A61B 34/30;
(Continued)

(56) References Cited

U.S. PATENT DOCUMENTS 7,953,509 B2  5/2011  Murayama
8,226,072 B2  7/2012  Murayama
(Continued)

FOREIGN PATENT DOCUMENTS

CN  201559195 U  8/2010
CN  103692452 B  4/2014
(Continued)

*Primary Examiner* — Anita M King
(74) *Attorney, Agent, or Firm* — MEDLER FERRO WOODHOUSE & MILLS

(57) ABSTRACT

The invention relates to a support arm system (10) for movably holding at least one medical device, including at least one movably supported support arm (18, 20, 22, 24) which is configured to hold the at least one medical device, having at least one load detection device (26) which is configured to detect the respective load data of the support arm system (10) during usage thereof; in particular configured by moving the support arm (18, 20, 22, 24), and which is formed with at least one storage device (46) which is configured to store the detected load data. Further, the invention relates to a method for operating a support arm system (10) and method for designing a support arm system (10).

12 Claims, 1 Drawing Sheet

(51) Int. Cl.
*A61B 90/35* (2016.01)
*A61B 90/50* (2016.01)
*B25J 9/16* (2006.01)
*G01B 5/008* (2006.01)
*G05B 19/00* (2006.01)

(52) U.S. Cl.
CPC ............... *B25J 9/16* (2013.01); *G01B 5/008* (2013.01); *G05B 19/00* (2013.01); *A61G 2203/32* (2013.01); *A61G 2203/36* (2013.01); *A61G 2203/726* (2013.01)

(58) Field of Classification Search
CPC .. A61B 90/50; A61B 90/35; B25J 9/16; B25J 1/00; B25J 13/08; G05B 19/00
See application file for complete search history.

(56) References Cited

U.S. PATENT DOCUMENTS

| | | | |
|---|---|---|---|
| 8,392,024 | B2 | 3/2013 | Murayama et al. |
| 9,367,061 | B2 | 6/2016 | Miller et al. |
| 9,757,297 | B2 * | 9/2017 | Arespong ............ A61G 7/1061 |
| 10,420,690 | B2 | 9/2019 | Dixon et al. |
| 10,451,217 | B2 | 10/2019 | Ravalitera et al. |
| 10,766,138 | B2 | 9/2020 | Perplies et al. |
| 10,989,354 | B2 * | 4/2021 | Erens ................... A61B 50/28 |
| 11,293,631 | B2 * | 4/2022 | Strölin ................... F21V 21/28 |
| 11,446,193 | B2 * | 9/2022 | Kaikenger ............ A61G 7/1017 |
| 2003/0086749 | A1 * | 5/2003 | Oliver ................ F16L 37/0841 403/13 |
| 2005/0075739 | A1 | 4/2005 | Nishizawa |
| 2005/0166413 | A1 | 8/2005 | Crampton |
| 2005/0222714 | A1 | 10/2005 | Nihei et al. |
| 2013/0221183 | A1 | 8/2013 | Volkenand et al. |
| 2013/0338430 | A1 | 12/2013 | Volkenand et al. |
| 2014/0020175 | A1 * | 1/2014 | Dixon .................... G16H 40/63 5/85.1 |
| 2015/0290809 | A1 | 10/2015 | Nakagawa et al. |
| 2016/0052128 | A1 | 2/2016 | Zimmermann et al. |
| 2016/0059407 | A1 | 3/2016 | Sonoda |
| 2016/0296297 | A1 | 10/2016 | Perplies et al. |
| 2017/0095932 | A1 | 4/2017 | Murakami |
| 2017/0254709 | A1 | 9/2017 | Lauzier et al. |
| 2018/0066794 | A1 | 3/2018 | Okuda et al. |
| 2018/0259122 | A1 | 9/2018 | Reavill et al. |
| 2018/0296285 | A1 | 10/2018 | Simi et al. |
| 2018/0369044 | A1 * | 12/2018 | Lyckestig ............... B66C 23/48 |
| 2020/0188205 | A1 | 6/2020 | Mattias et al. |

FOREIGN PATENT DOCUMENTS

| | | |
|---|---|---|
| CN | 107072862 A | 8/2017 |
| EP | 2455053 A1 | 5/2012 |
| EP | 2671557 A1 | 12/2013 |
| EP | 2684549 A2 | 1/2014 |
| EP | 2873403 A1 | 5/2015 |
| EP | 3372189 A2 | 9/2018 |
| JP | 2009291363 A | 12/2009 |
| JP | 4443615 B2 | 3/2010 |
| JP | 4475339 B2 | 6/2010 |
| JP | 4508263 B2 | 7/2010 |
| WO | 2017125677 A1 | 7/2017 |

* cited by examiner

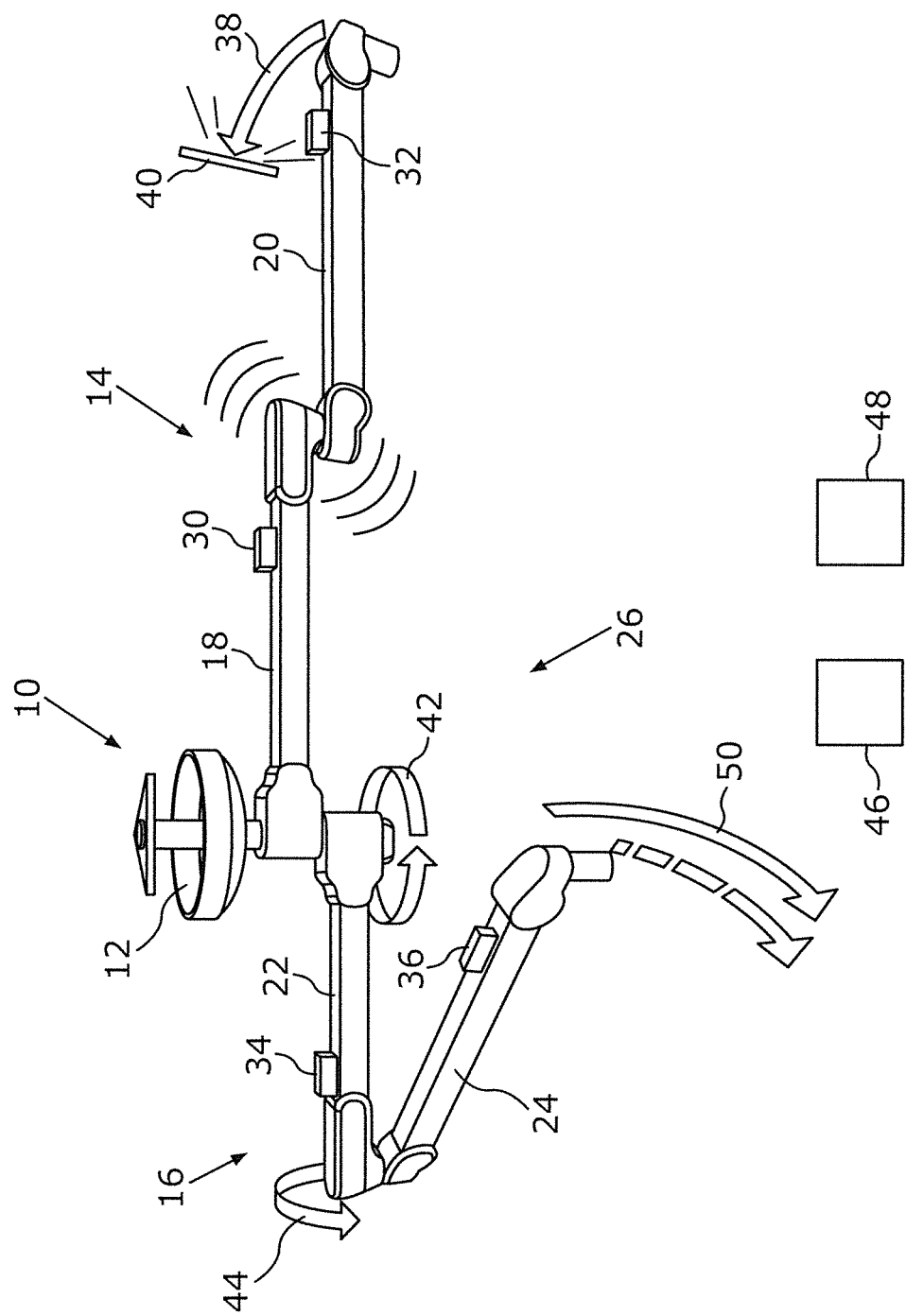

SUPPORTING ARM SYSTEM FOR A MEDICAL DEVICE, METHOD FOR OPERATING A SUPPORT ARM SYSTEM FOR A MEDICAL DEVICE, METHOD FOR OPERATING A SUPPORT ARM SYSTEM, AND METHOD FOR DESIGNING A SUPPORT ARM SYSTEM

FIELD

The present invention relates to a support arm system for movably holding at least one medical device, a method for operating a support arm system, and a method for designing a support arm system.

BACKGROUND

Support arm systems are for example used in surgery rooms for holding a medical device in a way that the position thereof may be altered. Hereto, a support arm may be movably anchored to a ceiling, a wall, or a floor by means of a bearing assembly, for example. It may also be mounted on a rack including wheels. Generally, support arm systems include at least one movable support arm for holding the medical device, which may also be denoted as medical engineering device, for example a surgical light, a surgical kit, or a dental drill set. Respective support arm systems may also comprise at least one brake device, which is configured to set a position of the support arm and thus of the medical device, and/or to inhibit respective movements of the support arm and thus of the medical device. A shift in position of the medical devices is vital for many medical procedures in order to facilitate the work of the medical staff or to enable it at all. Also, however any undesired shift of the device or even a breaking of the support arm system has to be strictly prevented so as not to potentially endanger the patient.

For example, a support arm system, which is denoted as a stand device, is known from WO 2016/026547, in which a force acting on the stand device is detected and depending thereon a brake for a support arm is activated and deactivated. Thus, a position of a medical engineering device may be set or the adjustment thereof may be released automatically. Due to said additional components, the support arm system is especially easy to use and safe during use. Here, also the safety for the respective patients and also for the medical staff using the stand device has to be ensured, of course.

This results in large safety margins in the design of such support arm systems regarding the load thereof, and frequent and extensive maintenance. Thus, appropriate support arm systems are expensive both in acquisition and also in maintenance. This relates to a high price of medical treatments or no such support arm systems will be provided at all, and this may limit the possibilities of medical treatments, especially in small hospitals or clinics. Alternatively, only simple, and thus inexpensive support arm systems may be provided, whereby however respective treatments are more complex to perform for the medical staff.

SUMMARY

It is an object of the present invention to reduce the costs of a support arm system for a medical device.

Said object is solved according to the invention by the subject-matters of the independent claims. Advantageous embodiments including appropriate further developments of the invention are specified in the respective dependent claims, wherein advantageous embodiments of an aspect are to be regarded as advantageous embodiments of respective other aspects and vice versa.

A first aspect of the invention relates to a support arm system for movably holding at least one medical device. The support arm systems may comprise at least one movably supported support arm, which is configured to hold at least one medical device. A connection between the support arm and the medical device may be fixed or releasable, and the device may also be part of the system. Preferably, the support arm system comprises a bearing assembly for movably supporting the support arm, for example by using a sliding bearing or roller bearing, using a rotary joint and/or a guiding rail. By means of the bearing assembly, the support may be anchored, for example on a wall, a ceiling, a rack including wheels, and/or further support arms. Correspondingly, also a plurality of bearings may be provided. The bearing assembly may also comprise a brake device to inhibit a movement of the support arm in an adjustable way, and/or to set it in a position in a selectable way. The at least one support arm may in particular be supported in a rotatably and/or translatory movable way using one or more degrees of freedom in movement. A movable support of the support arm may also relate to two support arms which are telescopically connected to each other. Additional support arms may be formed only indirectly for holding the medical device, by connecting the holding support arm to an anchoring, for example, and thus provide additional degrees of freedom.

In addition, the support arm system may comprise at least one load detection device which is configured to detect the respective load data of the support arm system during usage thereof, in particular by moving the respective support arm. However, usage may also relate to a stationary hold, wherein a time period and/or a load may also be detected. Normally, usage denotes the use of the medical device, for example for a medical treatment, which then causes a load on the support arm by moving and using the medical device. The detected load or the load data may for example allow to draw conclusions regarding wear and/or damage of the support arm system, whereby maintenance may be performed in a targeted way and/or a safety of the support arm system may be especially high, as also a hidden damage, as material fatigue, may be determined based on the load data in time, for example. The load data may for example correspond to a complete load of the system, which may also be denoted as aggregated load. Alternatively or in addition, the individual load of single components may be detected in order to maintain and/or replace them in a targeted way. For example, a support arm load of the respective support arm, and/or a bearing load of the respective bearing assemblies may be detected individually. In particular, respective loads may be only external, that is based on an external force impact, and in particular may comprise structural loads on single components and joints.

In addition, the support arm system may comprise at least one storage device, which is configured to store detected load data. This way, load data may be provided for later analysis. In particular, the manufacturer of the support arm system may collect load data from one or more systems, and configure a reworked design based on said data, thus it is especially cost-effective, lightweight, and requires only little maintenance. The load detection device and the storage device may thus be coupled to each other for data transmission, in particular wireless or by wire.

Here, storing is to be regarded as opposed to the detection of forces acting on the support arm system, which are then only used for controlling a component. For example, by means of sharing the detected load data, also a brake device of the support arm system may be controlled, for example, to inhibit or release the movement thereof, as required, wherein said data are however only available for further evaluation and/or any other usage after being stored. However, the support arm system may use sensors and/or detection devices to control the brake device to also detect load data, thus additional expensive sensors may be waived.

Preferably, the storage device is thus not only a temporary storage for data transmission and/or controlling or processing in a controller. Instead, the storage device is preferably configured to provide a long-term and permanent storage of the respective load data. For example, the storage device may comprise a RAM storage, a hard disk, and/or an optical drive. The storage device may also comprise an interface for data transmission to components external to the system. The load data may in particular correspond to a time profile of the load applied on the support arm system or the respective components thereof. In particular, in combination with the load data, a respective kind of use may be detected and stored, as for example the medical treatment performed here.

By using the support arm system and the respective stored load data, it is thus possible to determine, when a maintenance and/or replacement is required, in particular of respective specific components. During renovation projects of such a support arm systems, a successor support arm system may be provided based on the detected load data, being especially tailored to the requirement, and thus being cost efficient. Also, in the course of respective product developments, the respective stored load collectives may be taking into account in different applications. In addition, in case of respective complaints, it may be proven by the manufacturer by using the corresponding load data, if required, that the support arm system has not been operated correctly, and/or has been loaded in an incorrect way, in order to defend claims for damages. In addition, due to this, the system may be especially cost-efficient, as a risk of such claims has not be taken into account for the acquisition price anymore. In addition, respective load data may be used to recognize any incorrect operations, and to train the respective staff in the appropriate correct use in order to reduce wear. Also, a configuration which renders any respective misuse and/or incorrect operations impossible, is thus possible by a corresponding selection of other and/or additional degrees of freedom, for example.

The support arm system allows to overcome the disadvantages of traditional systems. A particular disadvantage was that no statement regarding the actual strain on the support arm system has been possible. Thus, it may be prevented that a support arm system is mounted in a room, and it may not be determined or only by an intensive elaborate inspection whether the support arm system has been heavily stressed and shows signs of wear, whether it was used in a wrong way and is damaged, or whether it has rarely been used, and thus provides almost the functionality of a new device. In addition, possible costs may be reduced, as by using the load data, the condition of the carrier system may be proven, and thus a higher price may be achieved for a used system on sale. In addition, for users like a hospital, an increase in efficiency during use may be achieved, as failure risks may be lowered, and/or a higher system availability may be ensured. This way, otherwise required reserve systems, which also require storage space, and also an extensive acquisition and storing of replacement parts may be waived.

A further advantageous embodiment of the support arm system provides that the support arm system further comprises an evaluation device which is configured to determine any required maintenance tasks for the support arm system depending on the stored load data. Thus, any required maintenance tasks may be automatically initiated. The maintenance requirements may in particular be determined depending on a time profile of the load, and/or an aggregated load. Maintenance requirements may for example relate to the replacement or repair of the support arm system or of single components, as for example, brake discs, bearings, or other wear parts, a readjustment of connections, as screw connections, and a lubrication of bearings, and/or due date of inspection.

Alternatively or in addition, the evaluation device may be configured to determine structural requirements regarding the design of a further support arm system, preferably for the same usage, depending on the stored load data, in particular depending on a time profile of the load and/or an aggregated load. The evaluation device may be configured to define the structural requirements regarding the design, for example by choosing a respective length of the support arm, the selection of the material of the structural components, the wall thickness, and/or the bearing (type). Thus, respective designs of support arm systems may be enhanced, and/or new layouts may be designed based on load data which are empirically determined in a comprehensive way. Thus, a test support arm system may also be used in order to subsequently determine the actual system depending on the test load data collected by the test support arm system. The later installed support arm system does not necessarily have to comprise the components for detecting and storing load data any longer. In particular, when determining structural requirements, it is also advantageous to detect and store the type of load. However, for other usage profiles, as for example in a hospital having another surgery focus, the structural requirements may then be determined by means of appropriate extrapolated loads based on load data which are assigned to stored device-specific load types in a very precise way.

The structural requirements may then refer to loads which a different or identical support arm system should be able to withstand. For example, in order to design a support arm system, the evaluation device may calculate a required resilience thereof using other components as joints or other parts, different degrees of freedom, and/or support arms having different lengths, based on the load data. The different geometry, degrees of freedom, and/or components may for example be selected by the evaluation device depending on the predefined constraints, as for example a size and partitioning of a surgery room, or may be specified by a designer. Correspondingly, in such other or modified support arm system other torques and/or bearing forces are acting which require a different structural design. The design may correspond to the respective requirements regarding the maximum and/or periodical load thereof, for example. Such a calculation may for example be performed by means of rigidity calculations or a simulation model, for example by using an CAD model. Likewise, regarding the structural requirements, different use constraints and thus the design may also be taken into account. For example, the design for a hospital having a larger or smaller capacity utilization, and corresponding to an increased or reduced frequency of use may be enhanced. Likewise, a higher lifespan and/or longer maintenance intervals may also be specified as constraints, wherein a respective load may be extrapolated from the stored load data for a modified time period. In addition, during an unexpected or early failure of the support arm system, for example due to material fatigue, changed structural requirements for a replacement support arm system may be calculated by using the load data to enable an enhanced design. The evaluation device may also be adapted as computer, for example.

The results of the evaluation may also be stored by the storage device in addition to the load data. The evaluation device may also be configured to evaluate load data immediately without storing it in advance. The storage device may then also store the results of said evaluation as load data. In said case, the evaluation results, as maintenance requirements, may also be considered as load data, in particular evaluated load data.

A further advantageous embodiment of the support arm system provides that a support arm system comprises a plurality of support arms being supported or arranged one adjacent to the other, wherein the load detection device is configured to detect the load for the respective support arms and/or the respective bearings individually. Respective support arms, which are movably supported adjacent to another, are preferably supported adjacently by means of assigned bearings which are sandwiched between them, respectively. Preferably, the storage device is configured to store respective load data individually, and/or to store the load data being assigned to the respective components of the support arm system. Due to a plurality of support arms, the support arm system may in particular comprise many degrees of freedom, hold a plurality of medical engineering devices, have an especially large range of motion, and/or may be especially well adapted to a complex room geometry and to further constraints, as further medical engineering devices which are arranged in the room.

A further advantageous embodiment of the support arm system provides that the load detection device is configured to detect respective absolute positions of the single support arms. This way, also stationary loads may be detected well, and the accuracy of the data may be particularly high. In particular, a one-time calibration of the respective sensors may be sufficient, if required.

A further advantageous embodiment of the support arm system provides that the load detection device is configured to detect respective positions of the single support arms relative to each other. This way, the load detection device and the respective sensors thereof may be especially simple and cost-efficient. In addition, a calibration may also be omitted, where appropriate. This is especially suited to detect loads due to acceleration in a cost efficient way.

A further advantageous embodiment of the support arm system provides that the load detection device is configured to detect respective movements and/or accelerations of single support arms. Thus, loads acting on single support arms may be detected in an individual and particularly precise way.

A further advantageous embodiment of the support arm system provides that the load detection device is configured to detect respective forces, in particular those which act on the individual support arms. Due to an immediate detection of force, a complex recalculation of loads may be omitted, where appropriate, thus the system requires less computing power, and the software thereof may be designed in a simple and cost-efficient way. In addition, the correspondingly detected external forces may simply be used for controlling further components, for example for driving actuators, and/or existing brake devices, if applicable.

A further advantageous embodiment of the support arm system provides that the load detection device is configured to detect vibrations, in particular those which single support arms and/or bearings are subjected to. Vibrations may be in particular important regarding wear, for example due to material fatigue, and a loosing of screw connections, and may allow in particular to draw conclusions regarding an incorrect use or incorrect operation, as hitting another object during movement, for example. Vibrations may also be indirectly detected by a force and/or acceleration measurements, wherein a high time resolution of the measurement may be useful, which may also be denoted as scan rate, for example.

The detections mentioned above may also be advantageously combined with each other, in particular in case the same sensors may be used or shall be used for different detections. Then, the support arm system is able to provide useful data regarding its daily use in a comprehensive and cost-efficient way.

A further advantageous embodiment of the support arm system provides that the load detection device comprises at least one sensor, in particular at least one sensor which is assigned to a support arm and/or to a bearing. The sensors enable an exact detection of individual load data. They may be arranged in an advantageously way due to the assigned sensors, for example at a position where the respective highest loads are to be expected or adjacent to regions and/or parts which are prone to incorrect usage or prone to damage, wherein the detected sensor data are particularly meaningful for load and/or maintenance requirements.

A further advantageous embodiment of the support arm system provides that the at least one sensor is configured as a force sensor, acceleration sensor, torsion sensor, torque sensor, position sensor, acceleration sensor, strain gauge, abutment sensor, GPS sensor, DGPS sensor, magnetic field sensor, brightness sensor, ultrasonic sensor, gyroscope, and/or pressure sensor. In particular, a plurality of assigned sensors of different types, for example a position sensor and an acceleration sensor, may be provided for each support arm and/or for each bearing. A sensor may also be formed as a combination of several types, for example, a strain gauge, which may also be arranged to detect a torsion. The at least one sensor may combine a plurality of sensor types, for example an acceleration sensor as movement and force sensor, in particular for an indirect detection, for example by means of recalculation.

The force sensor is especially suited for directly measure loads and also to detect stationary loads, for example held medical devices which are too heavy, having an overweight. An acceleration sensor is especially well suited for detecting movements and abutments and is cost-efficient and lightweight. A torsion sensor allows the detection of unusual misuse loads, like devices which are improperly held eccentrically, and an attempted enforcement of a movement beyond the movement range of the support arm system. A torque sensor is especially well-suited for detecting loads of the respective bearings. A position sensor facilitates to detect a movement profile of single support arms and to visualize stored load data. A strain gauge is able to detect a material fatigue very early and directly. An abutment sensor, which is for example formed as a button, allows to detect incorrect operations in an especially cost-efficient way. A GPS sensor or DGPS sensor is able to directly detect position data of single components, in particular independent of a calibration at site. In addition, also site data may be detected on the fly in order to be able to detect regional load differences, for example depending on the country, and to directly guide technicians for maintenance to the site of the respective support arm system. A magnetic field sensor may be especially cost-efficient, and may also be operated in a passive way, for example without power supply, and without a necessity of undesired electromagnetic interference, for example during usage next to imaging devices, like CTs, where applicable. A simple and cost-efficient example is a compass. This also applies for a brightness sensor, which is also able to detect distance measurements and thus impending collisions with other objects, for example things. An ultrasonic sensor is able to detect an impending collision with other objects in time, in order to activate a brake before collision, for example. This may also be used for detecting corresponding movements. A gyroscope enables an especially precise detection of position, and may also supply data for controlling a robot operation device. Pressure sensors are force sensors which enable to detect a two-dimensional load and thus enable additional load information.

A further advantageous embodiment of the support arm system provides that the load detection device, in particular the respective sensors thereof, is/are connected to the storage device for data transmission by means of wire or wireless. A cable-based data connection is especially robust and cost-efficient, and in addition consumes only little power. By means of a wireless data transmission, the configuration and movement of the support arm system or of the support arms is particularly free and the system is particularly lightweight. In particular, the load detection device may be configured to transmit load data to the storage device by using the Internet, and/or a mobile network, and or a telephone network. Thus, the storage device is no longer bound to the site of the further components of the support arm system, in particular of the respective support arms. This way, a further evaluation may be performed in a decentralized and independent way. For data transmission, the load detection device and/or the respective sensors may comprise an intermediate storage. Said storage may also be used to ensure redundant information, in particular during failure of the data transmission, and may also be regarded as part of the storage device. The data may be transmitted continuously or intermittently, for example.

A further advantageous embodiment of the support arm system provides that the storage device is formed as a centralized server, in particular for storing detected load data from the load detection devices from a plurality of support arm systems. The support arm systems may be configured as being identical or different. Thus, for example, respective load data may be collected and stored at the manufacturer site or the maintenance staff site in a centralized way. In addition, the evaluation device may also be configured as a centralized server, wherein the centralized server may then be configured both as storage device and also as evaluation device. Thus, the system may be configured in an especially cost-efficient way, and may collect a large amount of load data. Preferably, the load data are then transmitted by using the mobile network, and/or the telephone network, for example via the Internet. This way, data transmission is performed in a timely and cost-efficient manner. Alternatively, also an intermittent physical transmission may be performed, for example by using a data medium or by reading out the load detection device at the site. This way, a connection to the mobile network or fixed line network may be waived.

A further aspect of the invention relates to a support arm load detection system comprising a plurality of support arm systems according to the first aspect of the invention, and a storage device for storing the load data of all support arm systems in a centralized way, and/or an evaluation device for evaluating load data of all used support arm systems of one or more user(s). This way, a respectively assigned storage device and/or a respectively assigned evaluation device may be omitted for a plurality of support arm systems. Such a support arm load detection system will be especially cost-efficient, as load data may be stored and processed or evaluated in a simple and centralized way.

A second aspect of the invention relates to a method for operating a support arm system for movably holding at least one medical device. The method may comprise at least the step of using the support arm system for holding a medical device. The usage may in particular relate to a movement of the held device and/or a usage during a medical treatment of a patient by using said device. Here, preferably, the movably supported support arm of the support arm system is moved with at least one medical device held thereon. The movement may be caused or may be triggered manually and/or by means of an actuator.

Further, the method for operating the support arm system may comprise at least one step of detecting respective load data of the support arm system during the usage thereof, in particular by moving the support arm. In a further step, the detected load data may be stored. Detection may be here performed by means of a load detection device of the support arm system, and/or storing by means of a storage device of the support arm system. In particular, this may be performed automatically, for example, the detected movement may trigger an automatic storing of the respective corresponding load data.

By means of such an operation, the support arm system may be maintained in a way in particular tailored to the requirements. In addition, subsequent system generations may be configured as advantageously adapted to the requirements, by means of the load data, as for example individual structural requirements may be evaluated and predicted for a later use based on the stored load data, thus they may be especially cost-efficient and require only little maintenance.

Preferably, the method according to the second aspect of the invention is configured and suited for operating a support arm system according to the first aspect of the invention. The features and advantages resulting from the support arm system according to the first aspect of the invention are set forth in the description of the first aspect of the invention, wherein advantageous embodiments of the first aspect of the invention are to be considered as advantageous embodiments of the second aspect of the invention and vice versa.

A further advantageous embodiment of the method for operating the support arm system provides that the respective maintenance requirements for the support arm system are determined depending on the stored load data, and alternatively or in addition structural requirements regarding the design of a further support arm system are determined depending on the stored load data, preferably for the same use. This may be performed by means of an evaluation device of the support arm system. In particular, this may be performed depending on a stored time profile of the load data or of the load. Said evaluation may be performed directly without previous storage, and/or the results thereof may be stored as evaluated load data, in particular by using the storage device.

A third aspect of the invention relates to a method for designing a support arm system for movably holding at least one medical device by means of a movably supported support arm. The method may comprise an installation of a test support arm system, which may also be denoted as a test system, including at least one movably supported support arm at the desired site, and/or for usage for the same intended use as the support arm system which is to be designed. The structural features of the support arm system to be defined may for example be selected from the group consisting of the length of the support arm, the wall thickness, a material selection of the respective structural components and/or bearing(type). The use site may be simulated, if required, in order to perform a test phase also at the manufacturer site. However, the test system is preferably installed at the client site of the support arm system to be designed, in particular in the surgery room, where the final system is to be used; advantageously for usage under application-specific conditions and medical treatments. A further step relates to the usage of the test support arm system, in particular for collecting data. During usage time, respective load data of the test support arm system are detected during the usage thereof, in particular a movement of the support arms thereof. The test support arm system may also be used under real life use conditions to detect load data. The detected load data of the test support arm system may be stored. The actual support arm system which will finally be provided for permanent use may then be designed depending on the stored load data of the test support arm system. Thus, the requirements, in particular structural requirements, may be determined. The design may in particular comprise one or more designs of the support arm system, the basic concept thereof, the design thereof and/or determination of requirements thereof, for example concerning structural load requirements, degrees of freedom, size, movement range, and the actual configuration, for example the rigidness of components to be assembled (for example, bearings or joints), or the selection of materials. The support arm system to be designed may thus be configured individually according to the requirements, and thus may be configured in a cost-enhanced way, in particular for a specific site and usage situation, and/or enhanced for a specific client and its requirements and usage.

The test support arm system may in particular be formed as support arm system according to the first aspect of the invention, and may be operated using the method according to the second aspect of the invention. The method according to the third aspect of the invention may also relate to a usage of the support arm system according to a first aspect of the invention and to a method according to a second aspect of the invention. The features and advantages resulting from the support arm system according to the first aspect of the invention and the method according to the second aspect of the invention are set forth in the description of the first and second aspect of the invention, respectively, wherein advantageous embodiments of the first and second aspect of the invention, respectively, are to be considered as advantageous embodiments of the third aspect of the invention and vice versa.

The support arm system to be designed may also be a support arm system according to the first aspect of the invention. Alternatively, the support arm system to be designed may also include a traditional system without load data detection. The test system and the support arm system to be designed may be similar or identical or may also be different regarding the structure thereof. For example, the test support arm system may have a higher number of degrees of freedom and a larger movement range, and in addition may be configured for very high loads to be able to support any potential client requirements during test usage. Depending on the detected and stored load data, it may then be determined—by using the detected data—how many degrees of freedom and which movement range are actually required or make sense economically for the support arm system to be designed in thus use case, and/or which loads it has to support during real-life use, in order to subsequently design the support arm system for the client in an accordingly enhanced way.

BRIEF DESCRIPTION OF THE DRAWINGS

Further features of the invention become obvious from the claims, the exemplary embodiment, and the figures. The features and the combination of features mentioned in the specification above and the features and combination of features mentioned in the exemplary embodiments in the following may not only be used in the respective specified combination, but also in other combinations within the scope of the invention.

The FIGURE illustrates a support arm system including a load detection device.

DETAILED DESCRIPTION

The FIGURE schematically illustrates a support arm system 10 which is fixedly mounted on the ceiling of a surgery room by means of the anchoring 12. Two branches 14, 16 for respectively holding a medical engineering device are arranged on the anchoring 12 in a rotatable way, for example by means of a ball bearing. The first branch 14 comprises a first support arm 18 which is directly supported on the anchoring 12 in a pivotable way. The pivot movement is illustrated by arrow 42. To said first support arm 18 a second support arm 20 is connected, which is also connected to the first support arm 18 by means of a bearing for pivoting the two support arms 18, 20 relative to each other. On the end of the second support arm 20 opposite to the first support arm 18, a medical engineering device (not shown) is mounted, here, by means of a ball joint. The device may for example be a surgery light. The first branch 14 thus has two rotational degrees of freedom for moving the support arm 18, 20, and the medical engineering device may be moved due to the ball joint having further degrees of freedom. Thus, a surgeon may adjust the lightning of the operating table in a very unrestricted and precise way.

The second branch 16 comprises a configuration similar to the first branch 14. The second branch 16 comprises a third support arm 22, and a fourth support arm 24. The third support arm 22 is directly supported below the first support arm 18 on the anchoring 12, also in a pivotable way. The pivot movement is also illustrated by arrow 42. On the third support arm 22, the fourth support arm 24 is also supported in a pivotable way. On the end of the fourth support arm 24 opposite to the third support arm 22, a medical engineering device (not shown) is mounted, here, by means of a tilting joint. Thus, a tilting of the medical device in relation to a horizontal may be adjusted in a simple and comfortable way. This way, on the second branch 16, also a holder for the surgery kit, may thus be held as a device, for example.

Furthermore, one, more or all of the bearings may comprise a brake of a brake device, which is not shown here. Thus, a movement of the support arms 18, 20, 22, 24 relative to one another, and to the anchoring 12, as well as a movement of the two medical devices may be inhibited or prevented. By means of the brake it may also be ensured that the support arm system 10 is kept in a set position.

Obviously, the support arm system 10 is prone to wear by movement of the single components and also by opening and closing the brakes, and thus a respective activation and deactivation of the inhibition of the movement, which requires maintenance and/or inspections. Here, requirements regarding a support arm system for medical engineering devices are especially high, as a malfunction, as a lock or breaking of the support arm, may endanger a patient in the surgery room or may impact the surgery process. In addition, wear may also impact the hygiene of a surgery room in a negative way, for example, by falling down brake dust. In addition, the support arm system 10 may experience incorrect operations in a way that it unintentionally hits against other objects in the surgery room, for example. Also, incorrect usage loads, as an unallowed leaning of a surgeon against one of the branches 14, 16 may damage the support arm system 10 and/or may require a maintenance.

Due to this reason, the structure of traditional support arm systems is designed by using high safety margins, and they have to be inspected and maintained often and in a complex way. The high safety margins require expensive and clumsy systems. The elaborate maintenance and inspection result in high running service costs of the support arm system.

However, in the present embodiment, the support arm system comprises a load detection device 26 by means of which respective load data of the support arm system 10 may be acquired during the usage thereof, in particular during moving and/or stressing (loading) the branches 14, 16.

Hereto, the load detection device 26 comprises a first sensor 30 which is configured as acceleration sensor, and is arranged next to the connection to the second support arm 20 on the first support arm 18 or next to the bearing thereof. By means of the first sensor 30, thus a movement of the first support arm 18 may be detected. In particular, the first sensor 30 may be configured as highly sensitive, if required, thus it is able to also measure the vibrations of the bearing between the first support on 18 and the second support arm 20. Therefore, the sensor 30 may have a high scan rate, and may be configured to detect also short and/or very small accelerations. By means of said detection, conclusions may be drawn regarding a load of said bearing and also of the first support arm 18 and the bearing thereof on the anchoring 12.

Said detection and conclusions regarding the load may be further enhanced by means of the second sensor 32 on the second support arm 20. This may for example also be configured as acceleration sensor, whereby the movement of the two support arms 18, 20 may be detected separately from each other. In addition, an incorrect operation may be recognized by the second sensor 32, by hitting another object or a wall, for example. This is shown in the FIGURE by the arrow 38 and the object 40.

Analogous hereto, the second branch 16 comprises also a third sensor 34, and a fourth sensor 36. The third sensor 34 may for example be configured to detect a torsion on the bearing between the two support arms 22, 24 or a tilting, as it is illustrated by arrow 44. This way, load data regarding the weight of the device held on the second branch 16, and also load data regarding an incorrect leaning against it are available.

The fourth sensor 34 may be configured to detect a position of the joint for holding the medical device on a second branch 16, and thus detect a tilting against the horizontal, which is presently illustrated by arrow 50. Thus, the sensor 34 may also act as a trigger for an actuator, which automatically holds the medical device on the second branch 16 in the horizontal. In total, the respective sensors 30, 32, 34, 36 may also be configured to detect whether a user tries to move a part of the support arm system 10. Then an inhibition or lock of such a movement may automatically be deactivated by the brake device during such a detection, whereby the support arm system 10 is especially easy to use. After completion of the movement, the brake device may be automatically activated again.

For example, the sensors 30, 32, 34, 36 may also be formed as brightness sensors or magnetic sensors, and may detect the position and movement also by means of a change of brightness or a magnetic field. It is also possible to provide a compass as a sensor, which may then detect a pivot movement in the horizontal in a cost-efficient way.

The load data are transmitted from the load detection device 26 to the storage device 46. The storage device 46 may store the raw sensor data or may process them already in advance, that is, convert it in loads, for example, or both. Transmission may for example be performed wireless or by cable. By means of the storage device 46 load data are provided to determine whether a maintenance and/or a replacement of parts of the support arm system 10 is required, for example. This way, maintenance and replacement may be performed according to the actual individual usage and load of the support arm system 10 according to the requirements, which makes maintenance particular cost-efficient. Thus, for example, also hospitals may use the support arm 10, which only use a support arm system occasionally, whose low utilization and usage would otherwise not justify a standardized maintenance and replacement at regular intervals regardless of the actual load. In such cases, an acquisition would not be made because of regular (but unnecessary) maintenance and inspection costs for traditional support arm systems. In addition, the load data may be used for the design and construction of further developments or other support arm systems in order to further enhance them.

The support arm system 10 also comprises for the purposes mentioned above an evaluation device 48 by means of which respective maintenance requirements for the support arm system 10 may automatically be determined depending on the respective stored load data, and which also is able to determine structural requirements regarding the design of a further support arm system for the same use or for different uses depending on the stored load data, in particular by means of extrapolation. The evaluation device 48 may be connected to the storage device 46 for transmission of data via the Internet, for example, thus the evaluation device 48 does not need to be accommodated in the surgery room, but may be provided by means of a computer at the manufacturer site of the support arm system 10, for example. Likewise, the storage device 46 may also receive the sensor data via the Internet from the sensors 30, 32, 34, 36 which may comprise a mobile chip hereto, and/or may be connected to a shared transmission device. Thus, the storage device 46 and also the evaluation device 48 may be constituted together by a centralized server of the manufacturer. In particular, the storage device 46 and/or the evaluation device 48 may be configured to store and/or evaluate load data of a plurality of support arm systems 10 by means of load data detection, thus an especially large data base may be generated.

LIST OF REFERENCE NUMBERS

10 Support arm system
12 Anchoring
14 First branch
16 Second branch
18 First support arm
20 Second support arm
22 Third support arm
24 Fourth support arm
26 Load detection device
30 First sensor 32 Second sensor
34 Third sensor
36 Fourth sensor
38 Arrow
40 Object
42 Arrow
44 Arrow
46 Storage device
48 Evaluation device

The invention claimed is:

1. A support arm system (10) for movably holding at least one medical device, comprising
at least one movably supported support arm (18, 20, 22, 24) which is configured to hold at least one medical device,
at least one load detection device (26) which is configured to detect respective load data of the support arm system (10) during usage thereof, and
at least one storage device (46) which is configured for storing the detected load data,
wherein the support arm system (10) comprises a plurality of support arms (18, 20, 22, 24) which are supported adjacent to, and connected via a plurality of pivot bearings and/or tilting bearings to, one another such that the support arms pivot and/or tilt relative to each other, wherein the load detection device (26) is configured to individually detect the load for respective support arms (18, 20, 22, 24), and/or respective bearings.

2. The support arm system (10) according to claim 1, wherein the at least one load detection device (26) is configured for detecting respective load data of the support arm system (10) during moving the support arm (18, 20, 22, 24).

3. The support arm system (10) according to claim 1, wherein
the support arm system (10) further comprises an evaluation device (48) which is configured to determine the respective maintenance requirements for the support arm system (10) depending on the stored load data, and/or to determine the structural requirements for a design of a further support arm system for the same usage depending on the stored load data, in particular selected from the group consisting of a type of bearing, material selection of the structural components, wall thickness, and bearing structure.

4. The support arm system (10) according to claim 1, wherein
the load detection device (26) is configured to
detect respective absolute positions of the respective support arms (18, 20, 22, 24),
detect respective positions of the respective support arms (18, 20, 22, 24) relative to each other,
detect respective movements and/or accelerations of the respective support arms (18, 20, 22, 24),
detect respective forces, in particular those acting on the respective support arms (18, 20, 22, 24), and/or
detect respective vibrations, in particular those which the respective support arms (18, 20, 22, 24) and/or bearings are subjected.

5. The support arm system (10) according to claim 1, wherein
the load detection device (26) comprises at least one sensor (30, 32, 34, 36), in particular at least one sensor (30, 32, 34, 36) assigned to a support arm (18, 20, 22, 24) and/or to a bearing.

6. The support arm system (10) according to claim 5, wherein
the at least one sensor (30, 32, 34, 36) is configured as a force sensor, acceleration sensor, torsion sensor, torque sensor, position sensor, strain gauge, abutment sensor, GPS sensor, DGPS sensor, magnetic field sensor, brightness sensor, ultrasonic sensor, gyroscope, and/or pressure sensor.

7. The support arm system (10) according to claim 5, wherein respective sensors (30, 32, 34, 36), is/are connected by wire or wireless to the storage device (46) for data transmission.

8. The support arm system (10) according to claim 1, wherein
the storage device (46) is configured as a centralized server, in particular for storing detected load data of the respective load detection devices (26) from plurality of support arm systems (10).

9. The support arm load detection system comprising a plurality of support arm systems (10) according to claim 1, and a storage device (46) for storing the load data of all support arm systems (10) in a centralized way, and/or an evaluation device (48) for a centralized evaluation of load data of all support arm systems (10).

10. A method for operating a support arm system (10) of claim 1 for moveably holding at least one medical device, comprising at least the following steps:
moving of a movably supported support arm (18, 20, 22, 24) of the support arm system (10) including at least one medical device which is supported thereon;
detecting respective load data of the support arm system (10) based on the use thereof, in particular by moving the support arm (18, 20, 22, 24);
storing the detected load data.

11. The method according to claim 10, further comprising at least the following steps:
determining the respective maintenance requirements for the support arm system (10) depending on the stored load data,
and/or
determining structural requirements regarding the design of a further support arm system depending on the stored load data.

12. A method for designing a support arm system (10) for movably holding at least one medical device by means of a movably supported support arm (18, 20, 22, 24), comprising at least the following steps:
installing a test support arm system including at least one movably supported support arm at the desired site, and/or for usage for the same intended purpose as the support arm system which is to be designed;
usage of the test support arm system;
detecting respective load data of the test support arm system based on the use thereof, in particular by moving the support arm thereof;
storing the detected load data of the test support arm system; and
designing the support arm system (10) depending on the stored load data of the test support arm system.

* * * * *